US00PP07821P

United States Patent [19]

Nagare

[11] Patent Number: Plant 7,821

[45] Date of Patent: Mar. 10, 1992

[54] 'RED FRED' NECTARINE TREE

[76] Inventor: Fred K. Nagare, P.O. Box 848, Reedley, Calif. 93654

[21] Appl. No.: 544,859

[22] Filed: Jun. 27, 1990

[51] Int. Cl.[5] ..... A01H 5/00

[52] U.S. Cl. ..... Plt./41

[58] Field of Search ..... Plt./41, 40.1, 41.1, Plt./41.3

[56] References Cited

U.S. PATENT DOCUMENTS

P.P. 2,794 2/1968 Anderson ..... Plt. 41

P.P. 4,435 7/1979 Anderson ..... Plt. 41

*Primary Examiner*—Howard J. Locker

*Attorney, Agent, or Firm*—Worrel & Worrel

[57] ABSTRACT

A new and distinct variety of nectarine tree which is believed to be a mutation of the Early May Grand nectarine tree and is somewhat remotely similar to the May Grand nectarine tree of U.S. Plant Pat. No. 2,794 but from which it is distinguished by producing fruit which are mature for harvesting and shipment approximately one week later than the fruit produced by the May Grand nectarine tree and which fruit is more rounded, of superior firmness and exhibiting a superior color than the more yellow fruit of the May Grand nectarine tree.

1 Drawing Sheet

BACKGROUND OF THE NEW VARIETY

The present invention relates to a new and distinct variety of nectarine tree which will hereinafter be denominated varietally as 'Red Fred' and more particularly to a nectarine tree which is a mutation of the Early May Grand nectarine tree and which is patentably distinct therefrom in that it produces fruit which are mature for commercial harvesting and shipment approximately June 7 through June 12 in the San Joaquin Valley of central California, the fruit being of a semi-freestone type and the flesh of which is very firm and crisp.

The May Grand nectarine tree has for many years been the most popular nectarine tree having fruit which ripens in early June in the San Joaquin Valley of California. The developers of commercial varieties of fruit trees are continuously looking for new varieties which are not only hardy and tolerant of the growing conditions prevailing in fruit growing regions, but principally for new varieties which produce fruit which has superior characteristics as to flavor, firmness, shape, color, shaping quality and which ripen in growing periods not characterized by varieties producing fruit having equivalent characteristics. The variety of nectarine tree of the instant invention, although a mutation of the Early May Grand nectarine tree, is believed to have superior characteristics in these respects over known commercial varieties ripening for harvest in early June, including the May Grand nectarine tree. For purposes of clarity, it will be understood that while the 'Red Fred' nectarine tree of the present invention is a mutation of the Early May Grand nectarine tree, it is compared herein with the May Grand nectarine tree because it is most closely similar to the May Grand nectarine and that known variety of nectarine is the most extensively grown and therefore most readily available for comparison.

ORIGIN AND ASEXUAL REPRODUCTION OF THE NEW VARIETY

The present variety of nectarine tree was discovered by the inventor near Reedley, Calif. The inventor discovered the new variety as a sport of the Early May Grand nectarine tree in 1983 in his orchard of Early May Grand nectarine trees located at 14888 E. Dinuba Avenue, Parlier, Calif. The parent trees had been grafted to the Red Diamond variety of nectarine tree in 1981, but the sport was produced by the Early May Grand portion of the tree.

In 1985 the inventor asexually reproduced the new variety by grafting a number of nectarine trees to the new variety in his orchard located at 17305 E. Huntsman Avenue, Reedley, Calif. 93654 and has continuously observed the resulting trees of the new variety. The continued observation of the trees so asexually reproduced has confirmed that they have retained the distinctive characteristics, hereinafter set forth in greater detail, observed in the original sport.

SUMMARY OF THE NEW VARIETY

The 'Red Fred' nectarine tree is characterized as to novelty, and nonobviousness by producing a semi-freestone fruit which has a dark garnet-red to red-orange to more intense orange color which is ripe for commercial harvesting and shipment approximately June 7 through June 12 in the San Joaquin Valley of central California. The novel and nonobvious variety is most closely similar to the May Grand nectarine tree of U.S. Plant Pat. No. 2,794, but which is distinguishable therefrom and characterized principally as to novelty and nonobviousness by producing fruit which are ripe for harvesting and shipment approximately one week after the May Grand nectarine tree and which further produces a semi-freestone fruit which is of superior firmness, color and shape when compared with the fruit of the May Grand nectarine tree.

More specifically, the fruit of the 'Red Fred' nectarine tree of the present invention has an improved shape in that it is consistently more round than the rather elongate shape of the fruit of the May Grand nectarine tree. It is also of superior firmness in that the fruit of the May Grand nectarine tree tends to soften rapidly along the ventral suture which is not the case with the fruit of the instant variety. Furthermore, the fruit of the instant variety has superior color than that of the May Grand nectarine tree having a greater percentage of blush color than the more yellow "May Grand" fruit. The quality of the fruit of the two varieties is otherwise nearly equal.

BRIEF DESCRIPTION OF THE DRAWING

The drawing hereof displays typical specimens of the fruit and foliage of the instant variety, as grown in the San Joaquin Valley near Reedley, Calif. One nectarine of the new variety is oriented to show the stem cavity thereof; a second nectarine shows the apex; a third shows the suture; and a fourth has been sectioned to show the flesh thereof. A dry stone is shown together with foliage typical of the new variety showing leaf size, form and glandular characteristics.

DETAILED DESCRIPTION

Referring more specifically to the pomological details of this new and distinct variety of nectarine tree, the following has been observed under the ecological conditions prevailing at the orchard of origin which is located near Reedley, Calif. All major color code designations are by reference to the Dictionary of Color, by Maerz and Paul, Second Edition, 1950.

TREE

Generally:

*Size.*—Determined by pruning.

*Vigor.*—Vigorous.

*Figure.*—Upright spreading with eventual form and density determined by pruning.

*Productivity.*—Productive.

*Regularity of bearing.*—Regular.

*Strength.*—Hardy under normal climatic conditions prevailing in the San Joaquin Valley of California.

Trunk:

*Size.*—Medium.

*Surface texture.*—Average. Moderate amount of scarfskin present.

*Color.*—Ranges from light grey-brown (8-E-9) to a darker grey-brown (8-H-10).

*Lenticels.*—Numbers — numerous. Size — large.

Branches:

*Size.*—Average to slightly above average in thickness.

*Surface texture.*—Average.

*Color.*—Mature branches — Grey-brown (8-H-10) to dark brown (8-J-11). Immature branches with smooth surface texture — Pale green (20-J-5). Most exposed surfaces of young shoots tinged with red coloration as are the shoots in the photograph (5-H-8). Of course, the location of the shoots and leaves on a tree affect the coloration thereof.

LEAVES

Size:

*Generally.*—Large. Leaf measurements taken from leaves growing at midpoint of vigorous current season's shoots.

*Average length.*—18.4 cm (7.24 inches; 184 mm).

*Average width.*—4.7 cm (1.85 inches; 47 mm).

Leaf Thickness: Average for species.

Form: Lanceolate. Leaf apex acute and slightly twisted.

Color:

*Upwardly disposed surface.*—Medium green (23-L-6).

*Downwardly disposed surface.*—Grey-green (21-I-6).

Marginal form:

*Generally.*—Coarsely crenate with broad, low crenations.

*Leaf margin.*—Slightly undulate.

Glandular characteristics: Large in size, somewhat mixed in form. Reniform types predominate but a few globose glands can often be found. Gland location can also vary. Most often 4 to 5 glands present in alternate position on base of leaf margin with no glands present on leaf petiole. Considerable variation occurs however with up to 4 glands occasionally found on petiole and with only 1 or 2 present on the basal leaf margin. Gland color a shiny yellow-green (19-L-3) when young, darkening somewhat with age.

Petiole:

*Size.*—Medium.

*Length.*—8 mm (0.315 inches) to 12 mm (0.472 inches).

*Thickness.*—Average 2.0 mm (0.079 inches).

*Color.*—Green-yellow (19-J-5).

Stipules:

*Size.*—Medium, average 7.0 mm (0.276 inches) in length on vigorous shoots. Early deciduous.

*Form.*—Narrow lanceolate form with serrate margins.

*Color.*—Light yellow-green (17-K-4), darkening with age.

FLOWERS

Flower buds:

*Size.*—Medium and conic in form. Most frequently only one floral bud is present per node.

*Surface texture.*—Bud scales covered with a grey pubescence.

Flower bud scales — Color — Grey-brown (7-H-1).

Flowers:

*Generally.*—Non-showy type of bloom. Slightly above average in size for this type of bloom. Number of flowers somewhat light, or below average as compared with most other nectarine varieties.

*Date of bloom.*—Mar. 14, 1990. Medium to slightly late in comparison with the bloom of other commonly grown nectarine varieties.

*Size.*—Generally — Fully expanded flowers range in diameter from 20 mm (0.787 inches) to 23 mm (0.906 inches).

*Petals.*—Color — Light pink (1-E-2) on the interior portion of the petal and a darker pink (1-H-2) along the petal margins and on the claw. Petal color darkens to a rose color (1-I-3) with age, especially over the claw area. Size — Length — 13 mm (0.511 inches) to 15 mm (0.591 inches). Width — 9 mm (0.354 inches) to 11 mm (0.433 inches). Form — Oval to slightly obovate. Claw — size — medium. Claw — form — truncate. Apex is generally rounded and the margins are moderately undulate. The petals often remain somewhat rolled inward even at full maturity.

*Stamen.*—Length — 15 mm (0.591 inches) to 16 mm (0.630 inches) at full maturity. Stamen length equal to slightly longer than the pistil at full development. Color — Light pink (1-C-1) when young becoming darker to dark violet (4-J-3) with age.

*Pistil.*—Length — 14 mm (0.551 inches) to 15 mm (0.591 inches). Color — Green-yellow (17-K-2).

*Pistil surface.*—Glabrous.

*Pedicel.*—Length — Short average 2.0 mm (0.079 inches). Thickness — Medium average 1.5 mm (0.059 inches). Color — Light green (18-J-2). Surface — Glabrous.

*Nectaries.*—Color — Bright orange (11-K-12), becoming dull with advancing age.

*Anthers.*—Medium in size. Anther color ventrally tan (11-K-6), dorsally rust (5-K-11).

*Pollen.*—Abundant. Color — yellow (9-K-5).

FRUIT

Maturity when described: Firm commercial maturity with trees fully cropped. Ripe for commercial harvesting and shipment approximately June 7 through June 12, 1989 near Reedley in the central San Joaquin Valley of California.

Size:

*Generally.*—Large for season of maturity. Uniform.

*Average diameter in the axial plane.*—68.6 mm (2.70 inches).

*Average diameter in the suture plane.*—65.8 mm (2.59 inches).

*Average cheek diameter.*—67.2 mm (2.64 inches).

*Form.*—Slightly variable, ovate to nearly oval in lateral aspect. Nearly oval in apical aspect with slightly raised ventral suture. Symmetry — Most commonly symmetrical with one fruit half larger than the other. More round than the rather elongate May Grand nectarine tree.

*Suture.*—Generally — Shallow depression extending from base to apex along the ventral surface and over the apical shoulder on the dorsal surface. Suture color usually blends in well with the underlying dark red to orange blush color or ground color. Occasionally some dark red-orange (6-L-11) thin color stripes present along the suture line. Suture usually narrows and deepens over the basal shoulder of the ventral surface.

*Ventral surface.*—Generally — Variable. At times generally rounded while at other times slightly lipped on one side.

*Stem cavity.*—Generally — small. Width — Averages 24 mm (0.945 inches) to 27 mm (1.063 inches). Depth — Averages 14 mm (0.551 inches). Length — Averages 25 mm (0.984 inches) to 30 mm (1.181 inches). Shape — Oval with medium depth. Ventral suture open tightly folded within the cavity.

*Base.*—Slightly truncate. Base most often very slightly oblique to fruit axis.

*Stem.*—Average length 15 mm (0.591 inches). Medium thickness averaging 2.0 mm (0.079 inches) to 2.5 mm (0.098 inches). Color — Yellow-green (18-J-3).

*Apex.*—Shape — Generally rounded or very slightly raised.

*Pistil point.*—Oblique. Distinct depression beyond the pistil point opposite the ventral suture side. Numerous dots and flecking present, especially over the apical shoulders.

Skin:

*Thickness.*—Average. Tenacious to flesh at commercial maturity.

*Tendency to crack.*—Not observed.

*Blush color.*—Usually highly colored, 80 to 90 percent covered with a dark garnet-red (7-J-6) to red-orange (6-L-10) to more orangish (6-L-12).

*Ground color.*—Usually only present in low percentage, such as 2 to 5 percent, in and around the stem cavity. Ground color light yellow (9-K-2). Moderate flecking occurs over apical shoulders.

*Skin.*—Finish— Bright glossy.

*Flesh color.*—Uniform yellow-amber (9-K-4) from skin to pit cavity. Surface of pit cavity — Slightly darker than flesh (10-J-6) with no red coloration.

*Juice production.*—Juicy with maturity.

*Flavor.*—Excellent. Well balanced and pleasant.

*Aroma.*—Moderate.

*Texture.*—Firm, medium texture, becoming juicy with maturity.

*Fibers.*—Numbers — Moderate. Texture — Fine and same color as flesh.

*Ripening.*—Evenly throughout the fruit.

*Eating quality.*—Very good.

Stone:

*Attachment.*—Semi-free. Tightly held in pit cavity but eventually breaking free as fruit ripens.

*Fibers.*—Numbers — Few, mostly attached along ventral suture.

*Size.*—Length — Averages 38 mm (1.496 inches) to 41 mm (1.614 inches). Width — Averages 25 mm (0.984 inches) to 28 mm (1.102 inches). Thickness — Averages 19 mm (0.748 inches) to 21 mm (0.827 inches).

*Form.*—Generally — Oval to very slightly obovate.

*Apex.*—Shape — Generally rounded with a thin dentate and very acute tip. Size — 3 mm (0.118 inches) to 4 mm (0.157 inches) in length.

*Base.*—Shape — Most frequently rounded. Base angle most frequently at right angle to stone axis.

*Sides.*—Generally — Usually unequal.

*Hilum.*—Small, oval and substantially eroded.

*Stone surface.*—Very coarse with large rough ridges over the apical shoulders laterally and numerous irregular pits and grooves over the basal shoulders laterally.

*Ventral edge.*—A broad multi-ridged wing present from apex to base, most prominent over the basal shoulder.

*Dorsal edge.*—A broad moderately deep groove present from base to apical shoulder. Over the apical shoulder to the apex, the groove narrows and the shoulder becomes moderately broad.

*Ridges.*—Crossing the dorsal edge are rather large and jagged.

*Stone color.*—Dry color is a light brown-tan (11-H-6).

*Tendency to split.*—None observed.

Use: Fresh market nectarine for local use and long distance shipping.

Keeping quality: Good.

Although the new variety of nectarine tree possesses the described characteristics noted above as a result of the growing conditions prevailing near Reedley, Calif. in the central part of the San Joaquin Valley of central California, it is to be understood that variations of the usual magnitude and characteristics incident to changes in growing conditions, irrigation, fertilization, pruning and pest control are to be expected.

Having thus described and illustrated my new variety of nectarine tree, what I claim as new and desire to be secured by Plant Letters Patent is:

1. A new and distinct variety of nectarine tree substantially as illustrated and described and which is somewhat remotely similar to the May Grand nectarine tree of U.S. Plant Pat. No. 2,794 with which it is most closely similar but from which it is distinguished and characterized principally as to novelty and nonobviousness by producing fruit which are mature for commercial harvesting and shipment approximately June 7 through June 12 in the San Joaquin Valley of central California, or about one week later than the May Grand nectarine tree and have superior firmness, color and shape.

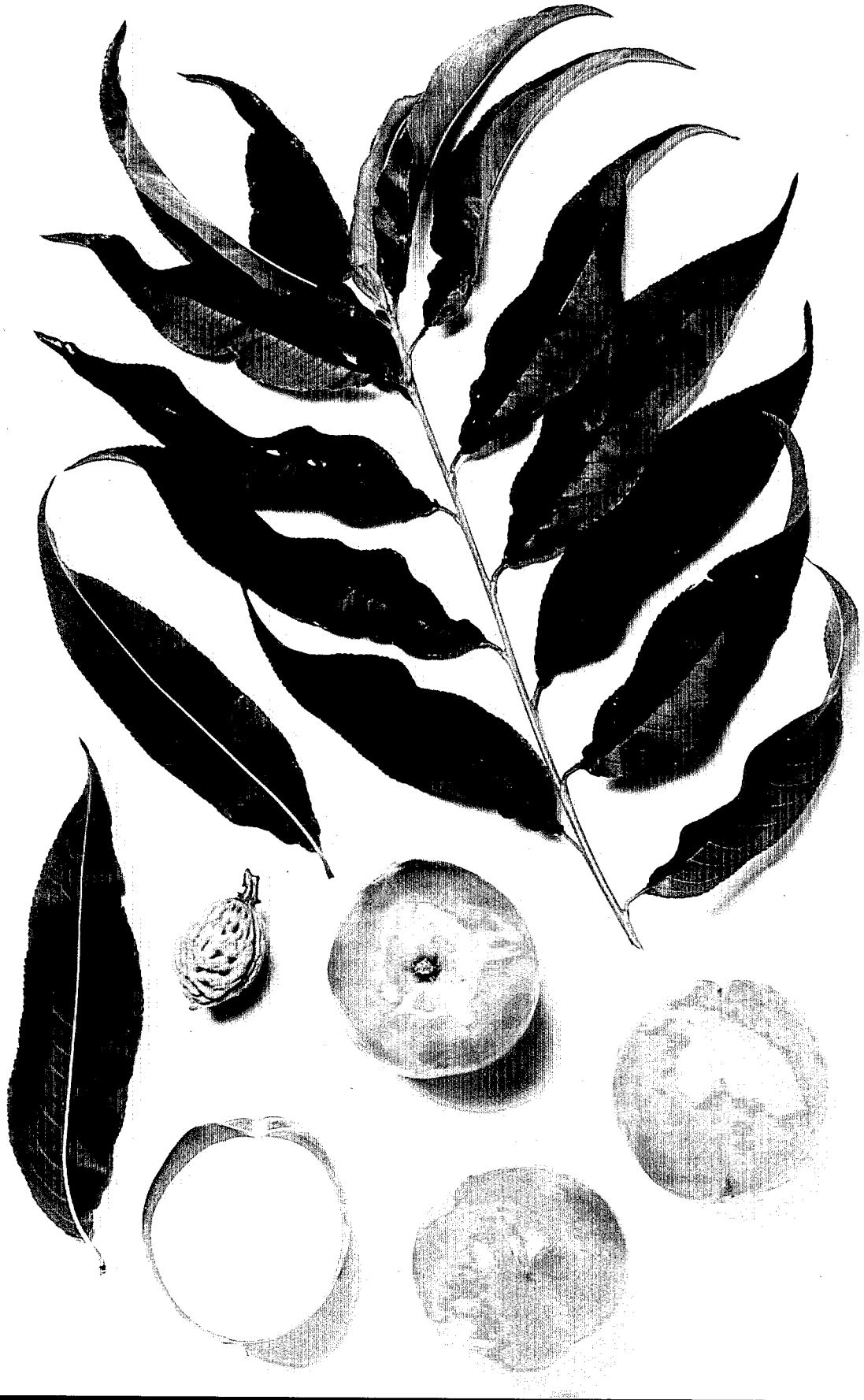

* * * * *